(12) United States Patent
Köpping et al.

(10) Patent No.: US 7,104,688 B2
(45) Date of Patent: Sep. 12, 2006

(54) DEVICE FITTABLE TO THE THERAPY HEAD OF AN X-RAY GUIDED LITHOTRIPSY SYSTEM TO ALLOW ADJUSTMENT OF THE FOCUS THEREOF

(75) Inventors: Heiko Köpping, Forchheim (DE);
Markus Lanski, Nürnberg (DE);
Matthias Mahler, Erlangen (DE);
Herbert Tauber, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 40 days.

(21) Appl. No.: 11/070,112

(22) Filed: Mar. 1, 2005

(65) Prior Publication Data
US 2005/0232398 A1 Oct. 20, 2005

(30) Foreign Application Priority Data
Mar. 1, 2004 (DE) .............. 10 2004 010 466

(51) Int. Cl.
*A61B 6/08* (2006.01)
(52) U.S. Cl. .................................... 378/205
(58) Field of Classification Search ............... 378/162, 378/163, 164, 204, 205, 207; 250/491.1
See application file for complete search history.

(56) References Cited

U.S. PATENT DOCUMENTS

| | | | | |
|---|---|---|---|---|
| 5,142,559 A | * | 8/1992 | Wielopolski et al. | 378/205 |
| 5,263,076 A | | 11/1993 | Elff et al. | 378/162 |
| 5,283,808 A | * | 2/1994 | Cramer et al. | 378/206 |
| 5,583,901 A | | 12/1996 | Reitter et al. | 378/4 |
| 6,267,502 B1 | * | 7/2001 | McNeirney et al. | 378/206 |

FOREIGN PATENT DOCUMENTS

| | | |
|---|---|---|
| DE | 40 03 350 | 4/1991 |
| WO | WO 2004/006786 | 1/2004 |

\* cited by examiner

*Primary Examiner*—Courtney Thomas
(74) *Attorney, Agent, or Firm*—Schiff Hardin LLP

(57) ABSTRACT

A device to adjust the focus position of the therapy head of a lithotripsy system having an x-ray system, has a cross-hair disc that can be attached to an image intensifier of the x-ray system, such that extending away from the edge of the cross-hair disc are variable-length connection elements whose outer end facing away from the cross-hair disc can be indirectly or directly affixed to the image intensifier.

17 Claims, 4 Drawing Sheets

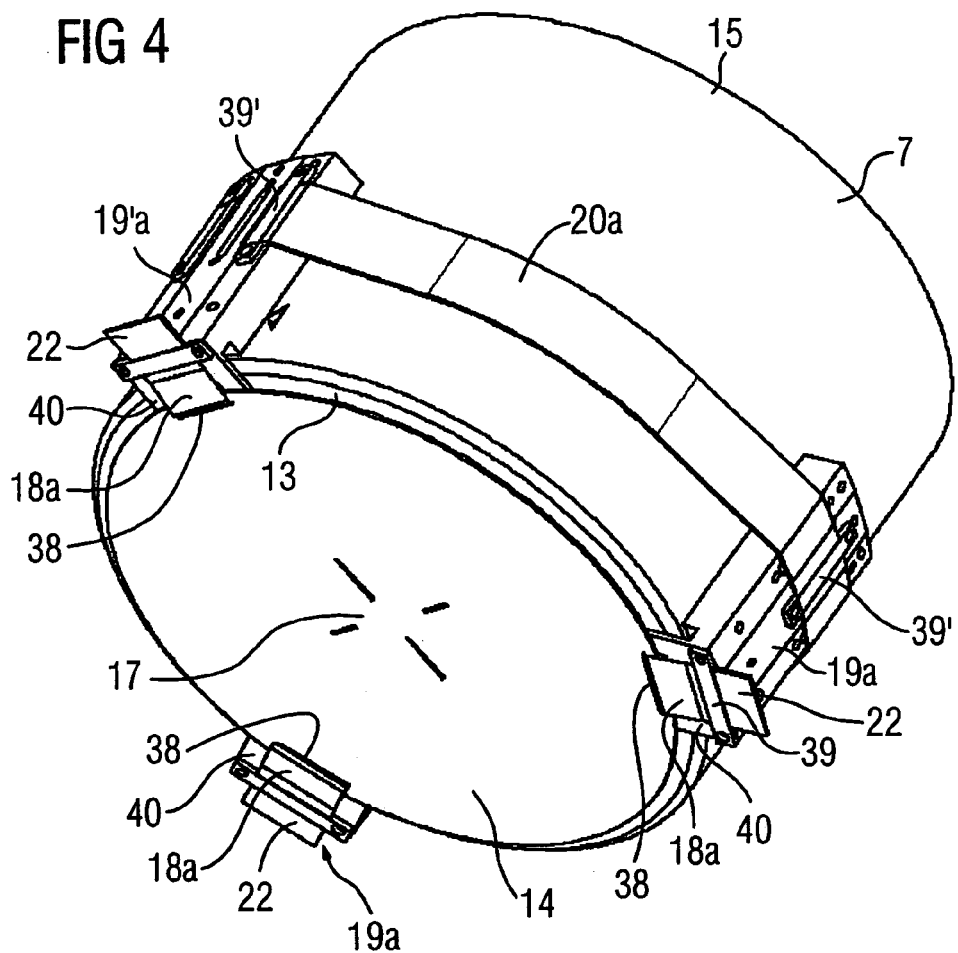
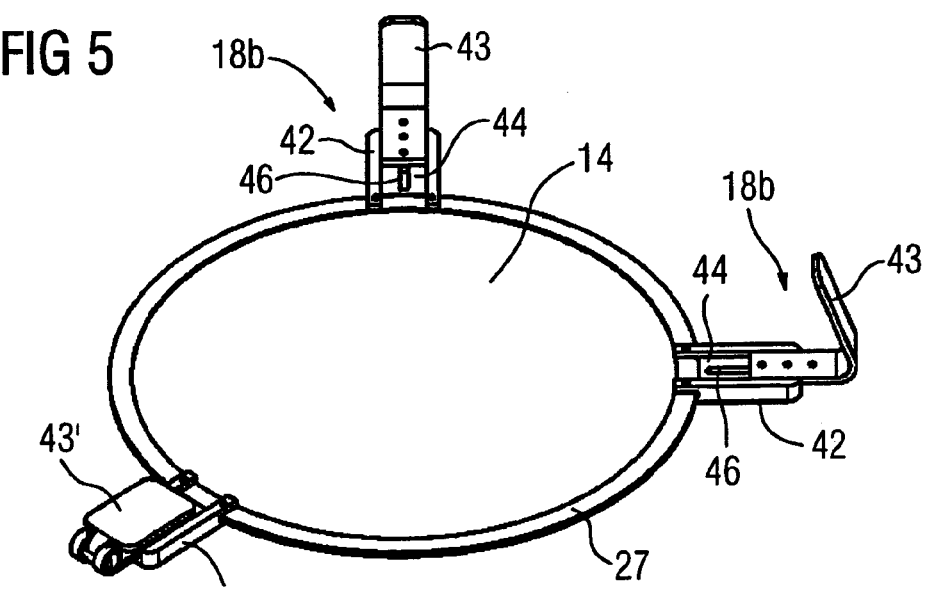

DEVICE FITTABLE TO THE THERAPY HEAD OF AN X-RAY GUIDED LITHOTRIPSY SYSTEM TO ALLOW ADJUSTMENT OF THE FOCUS THEREOF

BACKGROUND OF THE INVENTION

1. Field of the Invention

The present invention concerns a device for adjustment of the focus position of the therapy head of a lithotripsy system.

2. Description of the Prior Art

Adjustment of the position of the focus of the therapy head of a lithotripsy system can be accomplished using an x-ray system, usually in the form of a C-arm x-ray system. The x-ray system, having an x-ray source and an image intensifier, serves for imaging during a kidney stone treatment. For adjustment of (setting) the shockwave focus onto a central point detectable by the x-ray system from different angles, a target marking on the image intensifier of the x-ray system is necessary in the case of such a C-arm. This is the isocenter. A device serving for this purpose is a cross-hair disc that is affixed on the image intensifier with a fastening device. The target marking furthermore serves for positioning the shockwave focus in a stone to be treated. Such a cross-hair disc is formed of a material permeable to x-rays. A target or cross-hair made from a material that can be imaged in the image intensifier is disposed in its center. In the case of lithotripsy systems with an integrated x-ray system, the image intensifier is already provided at the factory with a cross-hair disc that is attached on the image intensifier such that cross-hair disc cannot be adjusted. To accommodate users undertaking only a small number of stone treatments, in more recent times the fixed mechanical coupling between the x-ray systems and the lithotripsy systems has been abandoned, particularly for cost reasons. Mobile lithotripsy systems are used that can be assigned to an arbitrary x-ray system via a mechanical interface. This allows the use of existing x-ray systems, used for other purposes, for lithotripsy as well. A problem, however, is the cross-hair disc is missing on the image intensifier, because the x-ray system is used otherwise.

SUMMARY OF THE INVENTION

An object of the present invention is to provide a device of the above-described type with which differently-configured image intensifiers can be retrofitted.

This object is achieved by a device according to the invention to the invention having, extending from the edge of the cross-hair disc, variable-length connection elements whose outer ends point away from the cross-hair disc, and that can be indirectly or directly affixed to the image intensifier. By means of the variable-length connection elements, an adaptation to image intensifiers with different diameters is possible, and thus retrofitting of practically any x-ray system can be achieved.

Given the attachment of a cross-hair disc, due to tolerance variations it may be necessary that a centering of the disc must be undertaken. In such a centering, the cross-hair center is caused to overlap the center point of the entrance surface of the image intensifier. The center point of the entrance surface often does not coincide with the geometric center point of the image intensifier housing. In a preferred embodiment, three connection elements are provided, preferably uniformly distributed around the circumference of the cross-hair disc. These allow a simple adjustment of the cross-hair disc in arbitrary directions, such that centering of the cross-hair can be effected in a simple manner dependent on the existing relationships.

In an embodiment, the outer end of the connection element is affixed on a mounting device attached to the outer circumference of the image intensifier. In another embodiment that involves little technical outlay a mounting element that can be affixed on the outer circumference of the image intensifier is associated with each connection element. The mounting elements are in turn affixed in a manner that can likewise be realized simply by a tightening strap (tensioning band) placed around the outer circumference of the image intensifier and clamping the mounting elements to the image intensifier. The mounting elements preferably are affixed to the image intensifier such that they can be detached. Even given a fixed connection between the cross-hair disc, the mounting elements and the connection elements, it is possible to remove the cross-hair disc from the image intensifier as needed. This is achieved in a particularly simple manner, without tools, when the tightening belt made from elastic material. It is naturally also be possible to affix the cross-hair disc to the connection elements such that it can be detached.

In a preferred exemplary embodiment, the length variability of a connection element is achieved by dividing it into a number of length sections demarcated from one another by predetermined breaking points. Each length section has a fixing element with which the connection element can be affixed on the edge of the cross-hair disc. Depending on the diameter of the image intensifier to be retrofitted, the connection elements are shortened by breaking off one or more length sections. Forming the fixing elements as a bore penetrating a length section ensures a simple attachment of the connection element on the edge of the cross-hair disc, which has bores at corresponding locations. The mechanical connection between these parts can ensue simply using screws or rivets. A snap connection between the outer end of a connection element and a mounting element ensures that the cross-hair disc can be removed from the image intensifier together with the connection elements affixed to the cross-hair disc. The entrance surface of the image intensifier, which faces an x-ray source, is then completely free of foreign elements. At most, mounting elements remain on the outer circumference of the image intensifier.

The aforementioned connection elements with predetermined breaking points allow a step-by-step adaptation to image intensifiers of different diameters. In this embodiment, however, a stepless (continuous) adaptation is possible by disposing an adjustment part between the outer end of a connection element and a mounting element. With this adjustment part, the distance between the connection element and the mounting element can be varied to an extent corresponding to the length of a length section that can be broken off.

In a further preferred exemplary embodiment, length variability of the connection element is achieved by forming the connection element of elastic material, so it is extensible in its longitudinal direction. The connection element is preferably affixed to the mounting element such that it can be detached. The elastic force and the gripping length of the connection element can be adapted to respective diameter ratios.

In a further embodiment, it is unnecessary to attach a mounting device on the outer circumference of an image intensifier. Rather, the affixing of the cross-hair disc ensues by fashioning the outer ends of the connection elements as hooks. The hook-shaped ends can be attached on the outer circumference of the image intensifier. The retention force necessary for a secure attachment is achieved by at least one hook-shaped end is that pre-stressed in the direction of the outer circumference surface of the image intensifier. Such a pre-stress is achieved by coupling a spring-loaded leg of flange, interacting with the outer circumference surface of the image intensifier, to the outer end of a connection element. By such a spring leg, in addition to a secure fastening a certain adaptation to differently-dimensioned image intensifiers is possible. This is achieved to an even greater degree in a preferred embodiment wherein a connection element has a first section affixed to the cross-hair disc and a second section formed by a hook-shaped end, and both sections can be affixed to one another in different longitudinal positions.

DESCRIPTION OF THE DRAWINGS

FIG. 4 is a perspective view of a first variant of the first embodiment.

FIG. 5 is a perspective view of a second variant of the first embodiment.

DESCRIPTION OF THE PREFERRED EMBODIMENTS

Figure 1:
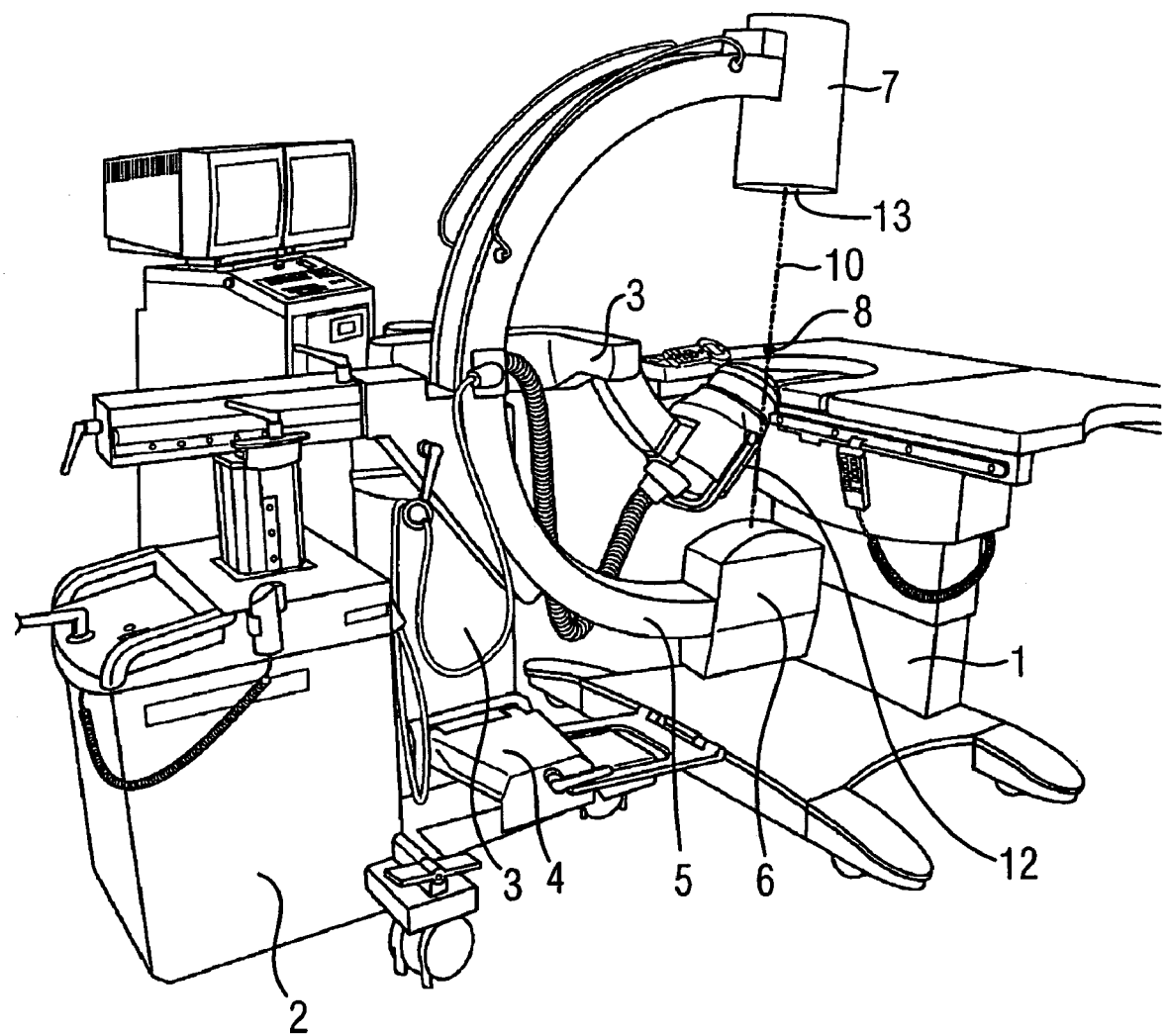
FIG. 1 shows a conventional lithotripsy system with an associated x-ray system.

FIG. 1 shows a lithotripsy system as is appropriate for a user with low demand for stone treatments. It has a mobile patient table 1, a mobile x-ray C-arm apparatus 2 that can also be used for other purposes, and a likewise mobile lithotripter 3. These assemblies are affixed to one another by a common mechanical interface 4. The x-ray C-arm apparatus 2 has a C-arm 5 with an x-ray source 6 mounted at one end thereof and an image intensifier 7 mounted at the opposite end. Before the implementation of a stone treatment, the focus point 8 of the therapy head 9 of the lithotripter 3 has to be adjusted such that it is intersected by a central beam 10 of the x-ray source 6, and so it is additionally arranged in the isocenter of the x-ray C-arm apparatus 2 or at least in the proximity thereof. To show the focus point, a folding (hinged) bracket or clip 12, that carries a metal ball visible in the x-ray image, is disposed at the therapy head 9. To adjust the focus point, a cross-hair disc 14 (not shown in FIG. 1) is necessary that is applied on the entrance surface 13 of the image intensifier 7. For systems used exclusively for lithotripsy, the image intensifier is already equipped at the factory with a removable cross-hair disc. For an x-ray C-arm apparatus 2 or another x-ray system that is used for other medical purposes, however, retrofitting with a cross-hair disc is necessary. Such a disc as well as a device with fastening elements is described in the following.

Figure 2:
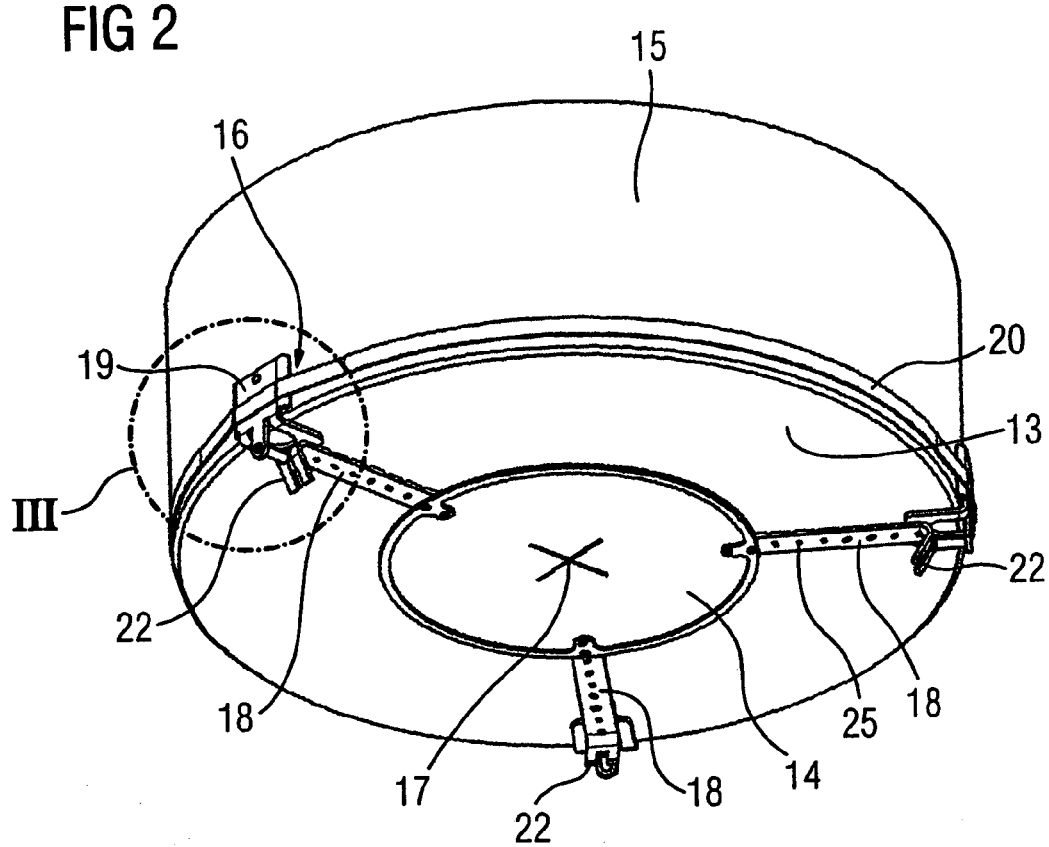
FIG. 2 is a perspective view of a first embodiment of a device for adjustment of the focus point of a shockwave head in accordance with the invention, the device being affixed to an image intensifier.
Figure 3:
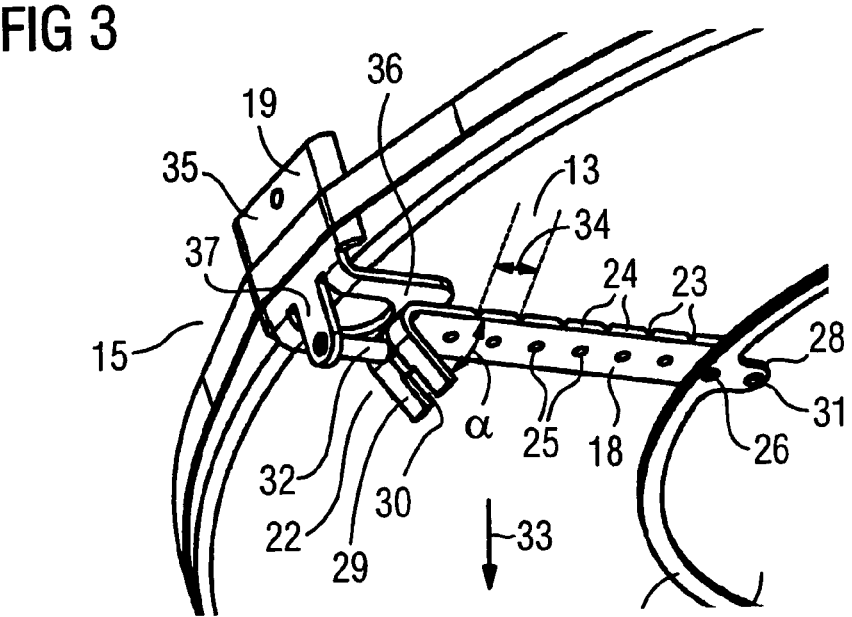
FIG. 3 shows the excerpt III from FIG. 2.

FIGS. 2 through 4 show two exemplary embodiments of a first device variant which involves a mounting device 16 that can be affixed to the outer circumference surface 15 of the image intensifier 7. In the mounted state (which is always referred to in the following) wherein the adjusted cross-hair disc 14 lies on the entrance surface 13 such that the cross-hair 17 that is present on it marks the entrance point of the central beam 10 or the x-ray-optical center of the entrance surface 13. The cross-hair disc 14 is connected with the mounting device 16 by connection elements 18 uniformly distributed around the circumference of the image intensifier 7. The mounting device 16 includes three mounting elements 19 clamped to the outer circumference surface 15 with a tightening strap 20, with which mounting elements 19 the radially outlying ends 22 of the connection elements 18 are mechanically coupled. The connection elements 18 are fashioned in strips and are produced from a solid material, such as aluminum plate. The connection elements 18 are divided into a number of length sections 24 separated from one another by predetermined breaking points 23 formed by notches proceeding transversely. By breaking one or more length sections 24, an adaptation to the respective diameter of the image intensifier 7 can ensue. Each length section 24 is penetrated by a bore 25 that serves to affix the connection element 18 to the cross-hair disc. This has a reinforced edge 27, for example likewise made from an aluminum material, in which a bore 26 is present. The fastening of the connection element 17 ensues, for example, by a screw (not shown) engaging through both bores 22, 26. In the region of the connection element 18, the edge 27 has a projection 28 directed radially inwardly, penetrated by a bore 31 and serving for affixing the cross-hair disc 14.

The outer end 22 of a connection element 18 is bent into a hook shape. The angle α between the curved section 29 and the remaining connection element is smaller than 90°. A central groove 30 proceeding in the longitudinal direction of the connection element 18 is present on the side of the section 29, pointing radially outwardly. A pressure (thrust) piece 32 affixed on the respective mounting element 19, engages in this groove with a catch element (not shown) spring-loaded in the engaging direction. The engagement point on the section 29 is positioned such that the end 22 of the connection element 18 is loaded (stressed) with a force directed toward the entrance surface 13, resulting from the oblique position of the section 29. To remove the cross-hair disc 14, the connection elements are removed from the image intensifier in the direction of the arrow 33. The application ensues in the opposite direction. The pressure piece 32 and the section 29 cooperate in the sense of a snap connection. With an adjustment screw 33, the spring-loaded catch piece engaging in the groove 30 in the radial direction can be adjusted by a range that approximately corresponds to the length 34 of a length section 24.

The mounting elements are plate pieces, designed as an angle section, with one leg 35 abutting the outer circumference surface 15 and with the other leg 36 abutting on the entrance surface 13 of the image intensifier 7. A clip 37 that carries the pressure piece 33 and extends the leg 35 over the entrance surface 13 projects from the leg 35. The leg 35 nearly abuts (with extended contact) the outer circumference surface 15 with curved side edges 41.

FIG. 4 shows an exemplary embodiment in which the connection elements 18a are produced from elastic material in the form of a band. Affixing to the cross-hair disc 14 can ensue by means of a slot 38 through which the radial inner end of the connection element 18a is guided to form a tab. The outlying end 22 is clamped to the mounting element 19a such that it can be detached. The clamping ensues via a web 39 extending away across the connection element 18a, the overhanging ends of which web 39 are screwed to the mounting element 19*a*. A certain margin in the adaptation to differently-dimensioned image intensifiers 7 exists solely via the elasticity of the connection elements 18*a*. The degree of the radial adaptation capability can still be increased by clamping the connection elements 18*a* to different longitudinal positions. By variation of the tension state or of the clamp position of individual connection elements 18*a*, centering of the cross-hair 17 on the center point of the entrance surface 13 is also possible in a simple manner. The mounting elements 19*a* are clamped via an elastic tightening strap 20*a* to the outer circumference surface 13 of the image intensifier 7. The tightening strap is clamped with its two ends to the outside of a mounting element 19' with the aid of two webs 39'. The remaining mounting elements 19*a* are affixed on the tightening strap 20*a* in the same manner, namely with a web 39'. In order to achieve a defined axial position for the mounting elements 19*a*, these exhibit a plate-shaped stop (catch) 40 extending radially inwards on their side facing the entrance surface 13. The plate-shaped stop 40 abuts the entrance surface 13 of the image intensifier 7.

Figure 6:
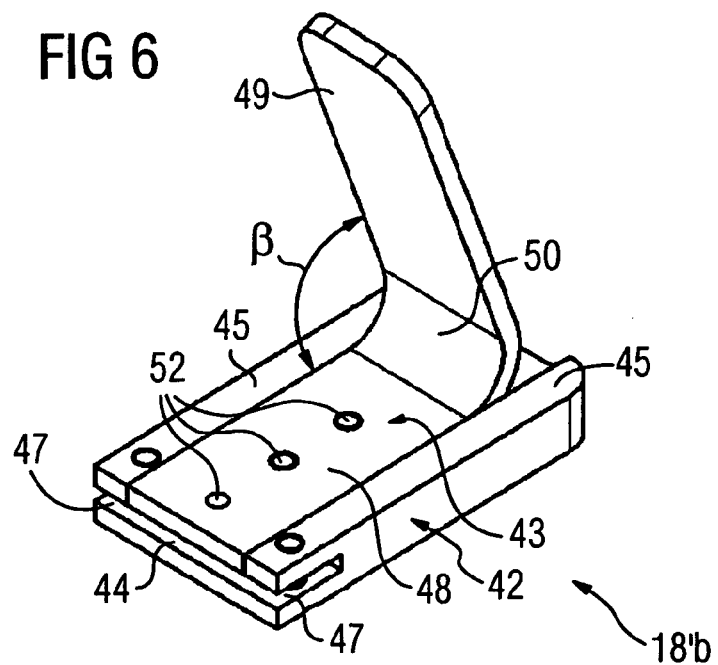
FIG. 6 shows a connection element of the device according to FIG. 5, in a perspective view.
Figure 7:
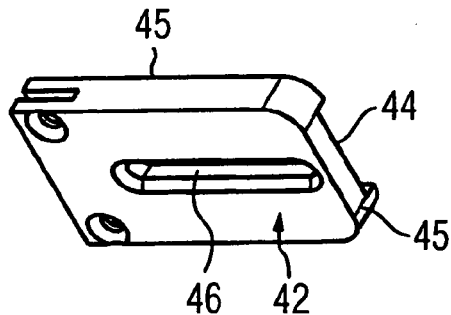
FIG. 7 shows a part of the connection element of FIG. 6, in a perspective view.

A variant is shown in FIG. 5 through 7 in which the fastening to an image intensifier 7 ensues with the connection elements 18*b* themselves. The connection elements 18*b* are formed by a first section 42 and a second section 43. The first section 42 is an essentially plate-shaped part with a rectangular contour shape. A recess 44 extending across its entire length is introduced onto its side facing the entrance surface 13 in the mounted state. The width of the recess 44 is less than the width of the first section 42, such that the recess 44 is flanked by two lateral edge strips. The first section 42 is furthermore penetrated by a centrally-arranged oblong hole 46 proceeding parallel to the lengthwise extent of the recess 44. A recess 47 that accommodates the edge 27 of the cross-hair disc 14 is present in the back side (facing the cross-hair disc 14) of the first section 42. In the region of the recesses 47, the edge strips 45 each have a bore 51 with which the section 42 can be affixed (screwed) to the edge 27.

Figure 8:
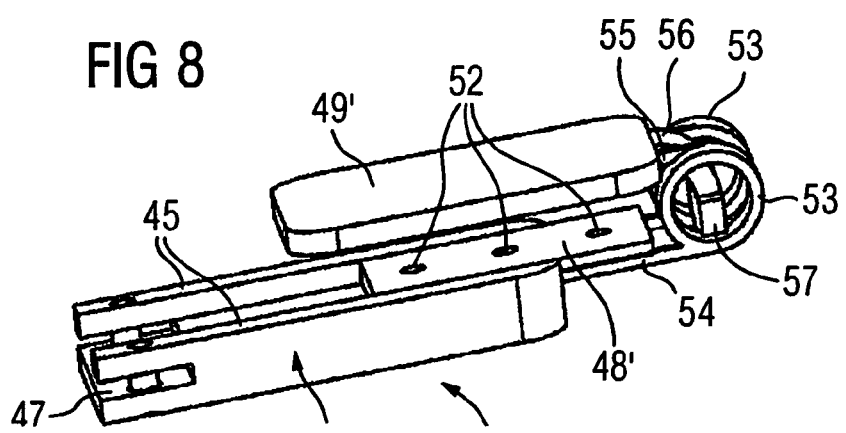
FIG. 8 shows a connection element of the device according to FIG. 5, with a spring-coupled leg.

The second section 43 is an elbow formed by two flat legs. With lateral guiding by the edge strips 45, the first leg 48 inserts into the recess 44 (lengthwise shifting), and the second leg 49 forms an angle $\beta$ (which is smaller than 90°) with the first leg 48. In the mounted state, the second leg 49 abuts on the outer circumference surface 15 of an image intensifier 7. Because the angle $\beta$ included by both legs is smaller than 90°, the second leg 49 abuts the image intensifier with only its free end. In the region of the groove (connecting both legs 48, 49) of the second section 42, in this manner a space is achieved that, for example, can accept an edge of the image intensifier, expanded like a bulge, that includes the entrance surface. The first leg 48 has a centrally-arranged series of threaded holes 52. A screw (not shown) engaging the oblong hole 46 is screwed with its thread end into at least one of the threaded holes 52. In this manner, the second section 43 can be affixed to the first section 42 in different longitudinal positions, and the device thus can be adapted to differently-dimensioned image intensifiers. One of the three connection elements 19*b*, namely that provided in FIG. 8 with the reference character 18'*b*, is designed such that it exerts a force on the outer circumference surface 15 of the image intensifier 7, and thus the remaining two connection elements 18*b* press on the circumference surface 15 of the image intensifier 7 with their two legs 49. Both legs 48' and 49' of the connection element 18'*b* are essentially designed the same, like the corresponding leg of the connection element 19*b*. However, the second leg 49' can pivot on the first leg 48' on an axis proceeding parallel to the planning level of the legs 48', 49'. Both legs 48', 49' are connected via two coaxial coil springs arranged next to one another. The respective outer spring ends 54 are connected with the leg 48' and the respective inner spring ends 55 are connected with the second leg 55. An axial separation into which protrudes an extension 56 formed on the back side of the leg 49', is present between the two leg springs 53. The extension 56 is shaped to a web 57 extending inwardly on both sides in the coil springs 53 within the leg springs 53. The web 57 serves for position fixing or as a pivot axle given a pivoting of the leg 49'.

A device or an add-on kit of the specified type can include a number of cross-hair discs 14 with different diameters so that, in addition to the length variability of the connection elements 18, a further adaptation to image intensifiers 7 of different sizes is achieved.

Although modifications and changes may be suggested by those skilled in the art, it is the intention of the inventors to embody within the patent warranted hereon all changes and modifications as reasonably and properly come within the scope of their contribution to the art.

We claim as our invention:

1. A device for assisting in adjusting a shockwave focus position of a therapy head of a lithotripsy system used with an x-ray system having an image intensifier with an entrance surface, said device comprising:
    a cross-hair disc; and
    a plurality of variable-length connection elements, each of said variable-length connection elements having an inner end attached at a peripheral edge of said cross-hair disc and an opposite outer end adapted for at least indirect affixing at a peripheral edge of said image intensifier, to position said cross-hair disc to visibly designate an x-ray-optical center of said entrance surface of said x-ray image intensifier.

2. A device as claimed in claim 1 comprising at least three of said variable-length connection elements, uniformly distributed around said peripheral edge of said cross-hair disc.

3. A device as claimed in claim 1 comprising, for each of said variable-length connection elements, a mounting device connected between said outer end thereof and adapted for attachment to said peripheral edge of said x-ray image intensifier.

4. A device as claimed in claim 3 wherein said peripheral edge of said image intensifier includes a circumferential side surface of said x-ray image intensifier, and wherein said mounting device includes a mounting element adapted to engage said circumferential surface.

5. A device as claimed in claim 4 comprising a tightening strap adapted for placement around said circumferential surface of said sidewall of said x-ray image intensifier to clamp each of said mounting elements against said sidewall.

6. A device as claimed in claim 5 wherein said tightening strap temporarily, detachably clamps said mounting element against said circumferential surface.

7. A device as claimed in claim 5 wherein said tightening strap is comprised of an elastic material.

8. A device as claimed in claim 1 wherein the outer end of each of said variable-length connection elements is adapted for detachably affixing at said peripheral edge of said x-ray image intensifier.

9. A device as claimed in claim 1 wherein each connection element comprises a plurality of length sections demarcated from each other by predetermined breaking points, with each of said length sections comprising an attachment element allowing attachment of the connection element at said peripheral edge of said cross-hair disc.

10. A device as claimed in claim 9 wherein said attachment element in each of said length sections comprises a bore penetrating through the length section.

11. A device as claimed in claim 1 wherein each of said variable-length connection elements comprises a snap connection at said outer end thereof and a mounting element snapped to said snap connection, said mounting element being adapted to engage said peripheral edge of said x-ray image intensifier.

12. A device as claimed in claim 1 wherein each connection element is comprised of a plurality of length sections demarcated from each other by predetermined breaking points, and a mounting element disposed at the outer end of said variable length connection element, said mounting element being adapted to engage said peripheral edge of said x-ray image intensifier and comprising an adjustment piece, connecting said mounting element to said outer end of said variable-length connection element, and allowing variation of a spacing between said mounting element and said variable-length connection element corresponding to a length of one of said length sections.

13. A device as claimed in claim 1 wherein each of said variable-length connection elements is comprised of an elastic material.

14. A device as claimed in claim 13 wherein the outer end of each of said variable-length connection elements is adapted for detachable affixing to said peripheral edge of said x-ray image intensifier.

15. A device as claimed in claim 1 wherein the outer end of each of said variable-length connection elements is hook-shaped, and wherein said hook-shaped end is adapted for engagement with said outer peripheral edge of said x-ray image intensifier, and wherein the hook-shaped end of at least one of said variable-length connection elements is pre-stressed in a direction of said peripheral edge of said x-ray image intensifier.

16. A device as claimed in claim 15 wherein said hook-shaped end comprises a spring-loaded leg adapted to interact with said peripheral edge of said x-ray image intensifier.

17. A device as claimed in claim 15 wherein each of said variable-length connection element comprises a first section affixed to said cross-hair disc and a second section formed by said hook-shaped end, said first and seconds being affixable to each other at selective, different longitudinal positions allowing selection of a degree of overlap between said first section and second section to vary the length of said variable-length connection element.

* * * * *